US006582684B1

(12) United States Patent
Abrahamson

(10) Patent No.: US 6,582,684 B1
(45) Date of Patent: Jun. 24, 2003

(54) BODY COATING COMPOSITION

(75) Inventor: Michael Abrahamson, Chicago, IL (US)

(73) Assignee: Xsight International, Chicago, IL (US)

( * ) Notice: Subject to any disclaimer, the term of this patent is extended or adjusted under 35 U.S.C. 154(b) by 0 days.

(21) Appl. No.: 09/889,358

(22) PCT Filed: Mar. 21, 2000

(86) PCT No.: PCT/US00/07467

§ 371 (c)(1),
(2), (4) Date: Sep. 4, 2001

(87) PCT Pub. No.: WO00/56274

PCT Pub. Date: Sep. 28, 2000

Related U.S. Application Data

(60) Provisional application No. 60/125,765, filed on Mar. 23, 1999.

(51) Int. Cl.[7] .................. A61K 7/04; A61K 7/021; A61K 7/025; A61K 7/06; A61K 31/74
(52) U.S. Cl. .................. 424/63; 424/61; 424/64; 424/70.1; 424/78.03; 424/401; 424/642
(58) Field of Search .................. 424/401, 63, 64, 424/61, 70.1, 78.03, 642

(56) References Cited

U.S. PATENT DOCUMENTS

| | | | |
|---|---|---|---|
| 4,184,977 A | 1/1980 | Eckstein et al. ....... | 252/301.22 |
| 4,534,961 A | * 8/1985 | Liff ............... | 424/63 |
| 5,830,446 A | 11/1998 | Berthiaume et al. ....... | 424/70.1 |
| 6,013,122 A | * 1/2000 | Klitzman et al. ........ | 106/31.03 |

FOREIGN PATENT DOCUMENTS

JP     407157759 A     6/1995

OTHER PUBLICATIONS

PCT International Search Report of PCT/US00/07467 dated Jul. 6, 2000.

* cited by examiner

Primary Examiner—Jose' G. Dees
Assistant Examiner—Marina Lamm
(74) Attorney, Agent, or Firm—Marshall, Gerstein & Borun

(57) ABSTRACT

A fluorescent and/or phosphorescent coating composition, particularly useful as a body coating, hair coating, lipstick and particularly as a phosphorescent nail polish that has the capability of changing from transparent, or other color, in light to a phosphorescing or fluorescing composition upon the withdrawal of light. The composition, e.g., nail polish, will return to its original color, as originally perceived by a human eye, as soon as light again contacts and is absorbed by the phosphorescent or fluorescent composition. The nail polish of the present invention is capable of undergoing a reversible chemical change upon the withdrawal of light without altering its physical properties.

18 Claims, No Drawings

BODY COATING COMPOSITION

CROSS REFERENCE TO RELATED APPLICATION

This application claims the benefit of provisional application Serial No. 60/125,765 filed Mar. 23, 1999.

FIELD OF THE INVENTION

The present invention is directed to a phosphorescent human body coating, particularly a nail polish, capable of phosphorescing a color when the phosphorescent composition is first exposed to a light source (i.e., sunlight or incandescent light) and then the light source is subsequently withdrawn from the phosphorescent composition (creating darkness)—the phosphorescent composition then phosphoresces. In a darkened environment, the nail polish phosphors a phosphorescent color and intensity, which are both dependent upon the type and concentration of fluorescent or phosphorescent agent used.

BACKGROUND OF THE INVENTION

The present invention is directed to a body coating that can be any desired color, or clear (transparent or translucent) in a lighted environment, particularly for fingernails and toenails, e.g. useful as a nail polish or for writing designs, words, pictures or other indicia on human skin, that has the ability to phosphoresce upon the withdrawal of a light source.

The process of luminescence occurs when an atom of a luminescent material absorbs a photon of energy. This forces the electrons into an excited state. As an electron moves from an intermediate energy state to its ground state, a photon (having a lower energy and frequency than the absorbed atom) is emitted from the atom. There are two basic types of luminescent substances, namely, fluorescent and phosphorescent materials. Fluorescent materials emit visible light after having been bombarded with ultraviolet radiation. Phosphorescent materials continue to glow long after an illuminating source has been removed since excited atoms may remain in a metastable state for several hours.

Predominantly, women use nail polish as a beauty accessory and often apply nail polish to match their clothing and/or lipstick—to enhance their appearance. Nail polishes are commercially available in varied colors and shades.

The phosphorescent nail polish and body coatings of the present invention are not toxic and do not cause skin irritation when the phosphorescent agents disclosed herein are combined with typical, commercial, nail polish components.

Accordingly, one aspect of the present invention is to provide a phosphorescent coating for human skin, hair and nails that is capable of absorbing light from a natural or synthetic light source, and continuing to emit a visible light therefrom after removal of the light source (in a darkened environment).

Another aspect of the present invention is to provide a method of applying a phosphorescent pigment- or dye-containing coating to human skin, hair, and/or nails (toenails and/or fingernails) that (after light absorption) will continue to emit a visually-detectable quantity of light such that an area of human skin, hair and/or nails coated with the compositions of the present invention can be readily seen in complete darkness for at least one minute, preferably longer.

The above and other aspects and advantages of the present invention will become more apparent from the following detailed description of the preferred embodiments of the present invention.

DETAILED DESCRIPTION OF THE PREFERRED EMBODIMENTS

While the present invention is susceptible of embodiment of various forms and will hereinafter be described in the form of the preferred embodiments, it should be understood that the following description of the preferred embodiments is to be considered an exemplification of the invention, and is not intended to limit the invention to the specific embodiments illustrated.

In accordance with the present invention, a phosphorescent composition, particularly useful as a body coating, hair coating, lipstick and particularly as a phosphorescent nail polish has the capability of changing from transparent, or other color, in light to a phosphorescing composition upon the withdrawal of light. The composition, e.g., nail polish, will return to its original color, as originally perceived by a human eye, as soon as light again contacts and is absorbed by the phosphorescent composition. The nail polish of the present invention is capable of undergoing a reversible chemical change upon the withdrawal of light without altering its physical properties.

In one embodiment, a phosphorescent agent is used, such as a zinc sulfide. Phosphorescent agents are available from United Mineral and Chemical Corporation of Lyndhurst, N.J. The phosphorescent agent(s) will exhibit various luminescent properties when subjected to ultraviolet light, sunlight, and/or artificial light from incandescent lamps. The human eye is most sensitive to yellow-green light within the spectral range from red to violet. Those skilled in the art will recognize that a variety of phosphorescent pigments of differing types can be used in the composition of the present invention.

Many phosphorescent compounds can be used successfully in the coating compositions of the present invention. The phosphorescent pigment or dye component of the compositions of the present invention includes one or more removable phosphorescent pigments, either organic or inorganic in structure.

Some suitable classes of fluorescent compounds useful alone or in admixture in the compositions of the present invention include the quinazolones, the oxazoles, the benzimidazoles, or the hydrazines; or classes of compounds represented by such compounds as the 1,8-dihydroxyanthraquinones, 4,5-diphenylimidazolones, p-methoxyphenyl-hydrazones, 6-hydroxynicotinic acids, salicylaldehyde semi-carbazones, 2-aminobiphenyls, 2-phenylbenzoxazoles, the class of bis (8-hydroxyquinolino) ZnII compounds, N,N"-bis-(salicylideneamino) oxamidenes, or the 1-cyanoformimidic acids. The following specific examples of fluorescent and phosphorescent compounds is indicative of the dyes and pigments which are expected to function suitably when used in the compositions of the present invention, and it is given by the way of illustration and not by way of 2 limitation.

2-(2-(napthylenesulfonylamino)phenyl)-4H-3,1-benzoxazin-4-one;

2-(1-(napthylenesulfonylamino)phenyl)-4H-3,1-benzoxazin-4-one;

2-(2-(p-toluenesulfonylamino)phenyl)-4H-3,1-benzoxazin-4-one;

2-(2-(o-toluenesulfonylamino)phenyl)-4H-3,1-benzoxazin-4-one;

2-(2-(2,4,6-trimethylbenzenesulfonylamino)phenyl)-4H-3,1-benzoxazin-4-one;
2-(2-(4-isopropylbenzenesulfonylamino)phenyl)-4H-3,1-benzoxazin-4-one;
2-(2-aminophenyl)-4H-3,1-benzoxazin-4-one;
2-(2-methyl aminophenyl)-4H-3,1-benzoxazino-4-one;
2-(2-mtsylaminophenyl)-4H-3,1-benzoxazin-4-one;
2-(2-(N-methyl-N-tosylaino)phenyl)-4H-3,1-benzoxazin-4-one;
2-(2-acet aminophenyl)-4H-3,1-benzoxazin-4-one;
2-(2-benzoyl aminophenyl)-4H-3,1-benzoxazin-4-one;
2-(2-benzenesulfonylaminophenyl)-4H-3,1-benzoxazin-4-one;
2-(2-(p-nitrobenzoylaminphenyl)-4H-3,1-benzoxazin,4-one;
2-(2-(p-nitrobenzenesulfonylaminophenyl)-4H-3,1-benzoxazin-4-one;
2-(2'-hydroxy phenyl)-benzimnidazole;
2-(2'-hydroxy phenyl)-benzoxazole;
2-(2'-hydroxy phenyl)-benzothiazole;
2-(2'-hydroxy-5'-aminophenyl)-benzothiazole;
2-(2'-hydroxy-3'-bromophenyl)-benzothiazole;
2-(2'-hydroxy-4'-bromophenyl)-benzothiazole;
2-(2'-hydroxy-5'-bromophenyl)-benzothiazole;
2-(2'-hydroxy-3',5'-di bromophenyl)-benzothiazole;
2-(2'-hydroxy-3'-chlorophenyl)-benzothiazole;
2-(2'-hydroxy-4'-chlorophenyl)-benzothiazole;
2-(2'-hydroxy-5'-chlorophenyl)-benzothiazole;
2-(2'-hydroxy-3',5'-dichlorophenyl)-benzothiazole;
2-(2',3'-dihydroxyphenyl)-benzothiazole;
2-(2',4'-dihydroxyphenyl)-benzothiazole;
2-(2',5'-dihydroxyphenyl)-benzothiazole;
2-(2',6'-dihydroxyphenyl)-benzothiazole;
2-(2'-hydroxy-3',5'-diiodophenyl)-benzothiazole;
2-(2'-hydroxy-3'-methoxyphenyl)-benzothiazole;
2-(2'-hydroxy-4'-methoxyphenyl)-benzothiazole;
2-(2'-hydroxy-5'-methoxyphenyl)-benzothiazole;
2-(2'-hydroxy-3'-methylphenyl)-benzothiazole;
2-(2'-hydroxy-4'-methylphenyl)-benzothiazole;
2-(2'-hydroxy-5'-methylpenyl)-benzothiazole;
2-(2'-hydroxy-3',5'-dimethylphenyl)-benzothiazole;
2-(2'-hydroxy-3'-nitrophenyl)-benzothiazole;
2-(2'-hydroxy-5'-nitrophenyl)-benzothiazole;
2-(2'-hydroxy-3',5'-dinitrophenyl)-benzothiazole;
2-(2'-hydroxy-5'-fluorophenyl)-benzothiazole;
2-(2'-hydroxy-4'-(dimethylamino)phenyl)-benzothiazole;
2-(2'-hydroxy-4'-(dietylamino)phenyl)-benzothiazole;
2-(2'-hydroxy-5'-acetamidophenyl)-benzothiazole;
2-(2'-hydroxy-5'-benzamidophenyl)-benzothiazole;
2-(2'-hydroxy-5'-benzylideneaminophenyl)-benzothiazole;
2-(2'-hydroxy-3',5'-bisphthalamidomethylphenyl)-benzothiazole;
2-(2'-hydroxyphenyl-3',5'-bisphthalimidomethyl)-benzothiazole;
2-(2'-hydroxy phenyl-3'-phthalimidomethyl)-benzothiazole;
2-(2'-hydroxy phenyl-5'-phthalimidomethyl)-benzothiazole;
4-(4'-dimethylaminobenzylidene)-2-phenyloxazolin-5-one;
(2-anilide-2',5'-dichlorobenzoylamino-1,9-anthapyrimidone;
bis-2,5-(benzoxazoyl)hydroquinone;
bis-2,5-(benzimidazoyl)hydroquinone;
bis-2,5-(benzothiazoyl)hydroquinone;
5-(4-(dimethylamino)benzylidene)barbituric acid;
sodium 3-(2-benzothiazolyl)-4-hydroxybenzene-sulfonate;
zinc sulfide doped with copper;
zinc sulfide doped with manganese;
zinc sulfide and cadmium sulfide doped with copper;
zinc sulfide and cadmium sulfide doped with silver;
sodium heteropolytungstate polyhydrate doped with europium;
zinc sulfide doped with calcium, cadmium, magnesium, molybdenum, and/or silicon;
cadmium sulfide doped with aluminum, calcium, magnesium, silicon, and/or zinc;
zinc selenide doped with aluminum, cadmium, and/or silicon;
cadmium selenide doped with aluminum, magnesium, silicon, and/or zinc;
calcium sulfide and strontium sulfide doped with heavy metals; and mixtures thereof.

The phosphorescent compositions of the present invention includes a phosphorescent compound in an amount of about 0.1 to 20 percent by weight of the coating composition (wet basis). To achieve, the full advantage of the present invention, the phosphorescent composition includes a blend of one or more phosphorescent pigments, at least one emulsifying agent capable of effectively dispersing the phosphorescent pigment in the coating composition, optionally a thickening agent for aiding in the long term suspension of the pigment(s), such as gums, clays or emulsion resins, and sufficient carrier (organic solvent and/or water, e.g., 25% to 80% by weight) to provide a dispersion having a phosphorescent pigment content of 1% to 75% by weight of the wet dispersion. In the dry coating composition, the phosphorescent compound comprises about 0.1% to about 25% based on the weight of solids in the dried composition. The particular emulsifying agent and thickening agent, e.g., resin, can vary depending upon the phosphorescent pigment utilized, however, examples of the emulsifying agent include glycols, polyols, or nonionic surfactants and examples of emulsion resins include polyacrylates, polymethacrylates, polyacrylic acids, polyacrylamides, and/or nitrocellulose. The phosphorescent composition also may include other optional components, including, but not limited to, defoamers, sequestering agents, preservatives and the like.

The body coating requires a phosphorescent pigment or dye; a resin or polymer capable of forming a continuous film; and a solvent (water or organic solvent) capable of evaporation to leave the remaining film. Some of the preferred resins, such as the fast drying nitrocellulose resins, require one or more plasticizers, such as dibutylphthalate to prevent embrittlement upon drying and to reduce shrinkage. Additionally, one or more adhesion resins may be included, such as a phenol formaldehyde resin, to provide good adherence of the composition to human skin, hair and/or nails. In the preferred embodiment, the plasticizer and phenol formaldehyde resin and nitrocellulose are wetted with wetting agents and carrier solvents, such as isopropyl alcohol and ethyl acetate or n-butyl acetate, which evaporate relatively quickly.

In the preferred embodiment, the phosphorescent agent is mixed with commercially available nail polish components—which include the following ingredients and amounts, by weight: nitrocellulose (5% to 30%), preferably 20%–30%, ethyl acetate (30% to 50%), preferably 30%–40%, butyl acetate (4% to 30%), preferably 8%–18%, and acetone (10%–20%). The nitrocellulose lacquer in the solvent is then mixed with one or more plasticizers and one or more adhesive resins. The preferred embodiment consists of LUSTRABRITE resin and CITROFLEX which can be varied by weight to obtain the desired viscosity, adhesive properties, flexibility and drying properties of the final product.

The phosphorescent agent is added in a proportion of about 0.1 % to about 70% by weight, preferably about 5% to about 60%, more preferably about 20% up to 40% of the total weight of the nail polish. The higher the concentration of the phosphorescent agent the more intense is the color phosphoresced. Phosphorescent pigments are stable in many water and solvent-based systems and the mixture with the nail polish is preferably at a neutral pH, e.g., pH 6–8, preferably 7, as opposed to an acidic mixture. Also the phosphorescent agent is best mixed with the nail polish slowly and gently as opposed to high speed mixing to avoid diminishing the "glow" properties.

Optionally, a colorant dye or pigment is added to the composition in any desired amount, e.g., 0.001% to about 5%, preferably 0.002% to 0.003% by weight (wet coating composition basis), to achieve any desired color, in addition to the phosphorescent property of the composition.

Suitable pigments include the Microsphere Fine Pigments (Red, Orange, Pink, and the like) from Radiant Color, a subsidiary of Magruder Color Co. It is preferred that the amount of colorant (dye and/or pigment) be included in the composition in an amount less than about 0.01% since higher loadings of colorant diminish the perceived light emission of the phosphorescent compound(s) in the composition.

The above is an example of this invention, and the example is not, in any way, limited to the above embodiments. The compatibility of phosphorescent agents is not limited to only the existing commercially available nail polish formulations but may be incorporated in any future development of formulations.

It is preferred to include an anti-settling agent or suspending agent in the composition in an effective amount to keep the solids, e.g. pigment, and phosphorescent agent(s), from settling in the composition. Anti-settling agents can have variable degrees of efficacious effect which is often dependent upon the interaction of the anti-settling agent with (1) the phosphorescent pigment used, and (2) the properties of the "solvent system". Suitable anti-settling agents include:

Acrylic/Acrylate Copolymers;
Ammonium Styrene/Acrylate Copolymer;
Ammonium Vinyl Acetate/Acrylate Copolymer;
Bentonite;
Corn Starch/Acrylamide/Sodium Acrylate Copolymer;
Polyethylene Glycol/Polypropyiene Glycol Copolymer;
Polyethyleneimine;
Polyacrylamidomethylpropane Sulfonic Acid;
Polychlorotrifluoroethylene;
Polyethylacrylate;
Ethylene/Acrylate Copolymer;
Ethylene/Maleic Anhydride Copolymer;
Ethylene/Vinyl Acetate Copolymer;
Hectorite;
Hydroxyethyl Polyethyleneimine;
Polyvinylpyrrolidone;
Polyvinylpyrrolidone/Eicosene Copolymer;
Polyvinylpyrrolidone/Ethyl Methacrylate/Methacrylic Acid Copolymer;
Polyvinylpyrrolidone/H exadecene Copolymer;
Polyvinylpyrrolidone/VA Copolymer;
Polyvinylpyrrolidone/Vinyl Acetate/Itaconic Acid Copolymer;
Sodium Butoxyethoxy Acetate;
Sodium $C_{4-12}$ Olefin/Maleic Acid Copolymer;
Stearalkonium Bentonite;
Stearalkonium Hectorite;
Stearyl vinyl Ether/ Maleic Anhydride Copolymer;
Isobutylene/Maleic Anhydride Copolymer;
Maltodextrin;
1-Methyl pyrrolidinone;
N-Methyl pyrrolidone;
Styrene/Acrylate/Acylonitrile Copolymer;
Styrene/Acrylate/Arnmonium Methacrylate Copolymer;
Styrene/Maleic Anhydride Copolymer;
Toluenesulfonamide/Formaldehyde Resin;
Vinyl Acetate/Crotonic Acid Copolymer;
Vinyl Acetate/Crotonic Acid/Methacryloxybenzophenone-1 Copolymer;
Vinyl Acetate/Crotonic Acid/Vinyl Neodecanoate Copolymer; and mixtures of any two or more of the foregoing.

The preferred anti-settling agent is DISPARLON 9030, a polyamide wax (30% by weight) in benzyl alcohol solvent (70% by weight).

The obtained formulation of phosphorescent nail polish is applied directly to the skin, hair and/or nails in any manner, e.g., by a brush, and allowed to air dry. Upon exposure to light, and then the subsequent withdrawal of light, the dried composition will phosphoresce (depending on the proportionate amount of phosphorescent agent) and then return to its normal state as soon as a light source is restored. The dried composition can phosphoresce a different specific color, upon the withdrawal of light, when a phosphorescent pigment with color specific phosphorescing characteristics is used (color specific phosphorescent pigments that phosphoresce a specific color upon the withdrawal of light are presently available from Allied Signal).

In accordance with one important embodiment of the present invention, the body coating composition of the present invention can be transparent in light, yet emit a clearly visible color when placed in darkness. The following "clear" or transparent composition is capable of being used as a conveyor of messages on skin, or for applying to nails, and dries to a clear lustrous film after application. Some color has been added so that the clarity of the film can be visualized. The film is resistant to removal by water. LAN ETO 50 is included for its lanolin-like attributes and inherent solubilization properties that assure clarity.

| INGREDIENTS | % W/W |
|---|---|
| Octylacrylamide/Acrylates/Butyl-aminoethyl Methacrylate Polymer | 25.00 |
| SD Alcohol 40 | QS 100.00 |
| Propylene Glycol | 2.00 |
| PEG-75 Lanolin* | 1.00 |
| D&C Red #22 | 0.50 |

* polyethylene glycol derivative of lanolin with an average of 75 moles of ethylene oxide.

Any of the above phosphorescent materials can be added to the above formulation, preferably in an amount of about 10–50% by weight of the composition.

Of course, those skilled in the art will appreciate that additional components can be included in the compositions of the present invention such as biocides, chelating agents, stabilizers, surfactants, solvents, defoamers, coalescing agents, and plasticizers. For example, KATHON CG brand of biocide can be included to preserve the composition during shipping by counteracting bacterial growth. Also, plasticizing agents can be included to provide appropriate coating formations on certain surfaces. Anti-foaming agents can be added to control foam formation during production and application. Stabilizers are commonly used to improve the freeze/thaw behavior of these types of coatings.

The preferred composition is as follows:

| I. Solvent/Film-Forming Resin/Plasticizer: | | |
|---|---|---|
| Components: | Preferred: | Range: |
| Ethyl acetate | 35% | 30% to 40% |
| Butyl acetate | 13% | 8% to 18% |
| Nitrocellulose (type: RS 1/4 second prewetted with 30% by weight isopropyl alcohol, from Hercules Corp.) | 25% | 20% to 30% |
| Lustrabrite resin* | 9% | 4% to 14% |
| Citroflex A4** | 3% | 2% to 7% |
| Acetone | 15% | 10% to 20% |

* an arylsulfonamide epoxy resin plasticizer
** acetyl tri-N-butyl citrate plasticizer by Morflex of Greensboro, North Carolina

| II. Glow And Anti-Settling Additives To Solvent: | | |
|---|---|---|
| Components: | Preferred: | Range: |
| Zinc Sulfide, Copper Doped (type: Hanovia, Series P3000) | 30% | 22% to 30% |
| Disparlon 9030* (Kusomoto Chemicals, Ltd. Tokyo, Japan) | 2% | 1% to 2% |

* a polyamide wax (30%) in a benzyl alcohol solvent (70%)

| III. Colorant Additive: | | |
|---|---|---|
| Colorant: | | |
| Microsphere Fine Pigment (Red, Pink, Orange, etc.) | 0.0025 % | 0.0020% to 0.0030% |

| III. Colorant Additive: |
|---|
| Colorant: |
| (Radiant Color, a subsidiary of Magruder Color Co.) |

Manufacturing Procedure

With reference to the above preferred composition listed above for "I. Solvent/Film-Forming Resin/Plasticizer": Activate the nitrocellulose, e.g., ¼ second wetted with 30% by weight isopropyl alcohol from Hercules Corp., place into a container, adding and mixing (use of an explosion proof agitator equipped with a stirrer capable of imparting relatively high shearing stress is recommended). Add the rest of the ingredients in order, and stir until a homogeneous dispersion with good thixotropy results to establish the solvent blend.

Add the copper doped zinc sulfide using minimal shear effect with continuous slow mixing to achieve adequate dispersion, (mixing for at least 10 minutes). Make certain the phosphorescent pigment is fully dispersed in the solvent.

Lastly, add the anti-settling agent, Disparlon 9030, to the solvent system, avoiding incorporation of air into the blend. The preferred method of addition of the Disparlon 9030 is to add it initially with the mixer shut off. This assists in not drawing air into the mixture. Continue to avoid introduction of air by using care in controlling the speed of the mixer so that excessive vortex of the solution is avoided. Initially the blend can be mixed for one minute by impeller blade (not exceeding 1000 RPM). Then for the next 10 minutes, the speed of the mixer impeller should be increased slightly (not to exceed 3000 RPM). Speed and mixing time can be adjusted depending upon resin mix and desired thixotropy. The controlling factor should always be to run the impeller blade at minimal speed without incorporating air. Strong "vortexing" of the mix is avoided during mixing to avoid air entering into the blend.

The final addition is the "III. Colorant Additive", listed above. The colorant additive is mixed in a minimal concentration amount; just enough to give the blend the desired daylight color without excessive addition of colorant additive (to avoid diminution of glow properties).

The above-described preferred coating composition has the following properties:

1. The solvent system has a good thixotropic consistency relative to
   (a) acting as a carrier for the "Glow Additives" and "Color Additives" and,
   (b) having good, fast drying characteristics.
2. In addition the composition has a short drying time and the surface of the film-forming resin, after drying, is smooth, yet hard.
3. The Copper Doped Zinc Sulfide phosphorescent material remains suspended in the solvents and should be added slowly while gently mixing. The Copper Doped Zinc Sulfide should be well "wetted-out" with the solvent by mixing for at least 30 minutes.
4. The anti-settling agent, e.g., Disparlon 9030, should be added slowly while gently mixing, avoiding the vortex of the blade and avoiding the introduction of air.

From the foregoing it will be observed that numerous modifications and variations can be effectuated without departing from the true spirit and scope of the novel concepts of the present invention. It is to be understood that no limitation with respect to the embodiment contained herein is intended or should be inferred. The disclosure is supportive of the non-provisional patent application.

What is claimed is:

1. A light-emitting coating composition for coating a human body part comprising a solvent; an emulsifying agent capable of dispersing a phosphorescent material in the coating composition; a film-forming resin capable of forming a continuous film upon solvent evaporation; an effective amount of an anti-settling agent; and a light-absorbing phosphorescent material in an amount sufficient to emit a visible amount of light after being contacted by light and then removing light from contacting said light-absorbing material.

2. The composition of claim 1, wherein the coating composition includes a phosphorescent material in an amount of about 0.001% to about 5% by weight, based on the total weight of the coating composition.

3. The composition of claim 2, wherein the coating composition includes a colored pigment in an amount of about 0.002% to about 0.003% by weight, based on the total weight of the coating composition.

4. The composition of claim 2, wherein the film-forming resin comprises nitrocellulose.

5. The composition of claim 4, wherein the film-forming resin comprises nitrocellulose, prewetted with an alcohol.

6. The composition of claim 4, wherein the light absorbing phosphorescent material is copper-doped zinc sulfide.

7. A method of coating a human body part such that said coated body part emits visible light after said coated body part is contacted by light and then said body part is disposed in a dark environment, comprising coating said body part with a composition comprising a solvent; a film-forming resin capable of forming a continuous film upon solvent evaporation; an effective amount of an anti-settling agent; a light-absorbing phosphorescent material dispersed in the composition; and evaporating the solvent to form a continuous film on said body part.

8. The method of claim 7, wherein the body part is selected from the group consisting of toenails, fingernails, a facial component and a combination thereof.

9. The method of claim 8, wherein the body part is a facial component selected from the group consisting of eyelids and cheeks.

10. The method of claim 7, wherein the body part is selected from human skin, and human hair, and the light-emitting coating composition is applied as a covering coat and said coating emits visible light when a wearer of said covering coat disposes himself in a dark environment.

11. The method of claim 7, wherein the body part is selected from human skin and human hair, and the light-emitting coating composition is applied as a conveyor of a readable message when the wearer of said message disposes himself in a dark environment.

12. The method of claim 7, wherein the coating composition includes a phosphorescent material pigment in an amount of about 0.001% to about 5% by weight, based on the total weight of the coating composition.

13. The method of claim 12, wherein the coating composition includes a colored pigment in an amount of about 0.002% to about 0.003% by weight, based on the total weight of the coating composition.

14. The method of claim 12, wherein the film-forming resin comprises nitrocellulose.

15. The method of claim 14, wherein the film-forming resin comprises nitrocellulose, prewetted with an alcohol.

16. The method of claim 14, wherein the light-absorbing material is copper-doped zinc sulfide.

17. A method of manufacturing a light-emitting coating composition for coating a human body part comprising:
mixing a solvent, an emulsifying agent and a film-forming resin to form a homogenous dispersion;
adding a phosphorescent pigment to the homogeneous dispersion and mixing for a time sufficient to fully disperse the phosphorescent pigment;
adding an anti-settling agent in an amount sufficient to prevent settling of the phosphorescent pigment, mixing initially at an impeller speed less than 1000 rpm, and then increasing the impeller speed to a speed not to exceed 3000 rpm.

18. A method of coating a human body part such that said coated body part emits visible light after said body part is contacted by light and then said body part is disposed in a dark environment, comprising coating said body part with a composition comprising a solvent; a film-forming resin capable of forming a continuous film upon solvent evaporation; an effective amount of an anti-settling agent; and a compound that is capable of absorbing light and then capable of emitting light when exposed to a dark environment, said compound dispersed in the composition; and evaporating the solvent to form a continuous film on said body part.

* * * * *